United States Patent [19]

El Bahy et al.

[11] Patent Number: 5,338,660
[45] Date of Patent: Aug. 16, 1994

[54] DIAGNOSIS OF FASCIOLA INFECTIONS BY DETECTION OF ANTIGENS IN FECES OR INTESTINAL CONTENT

[75] Inventors: Mohamed M. El Bahy, El Giza, Egypt; John B. Malone, Jr.; William J. Todd; Kenneth L. Schnorr, all of Baton Rouge, La.

[73] Assignee: Board of Supervisors of Louisiana State University and Agricultural and Mechanical College, Baton Rouge, La.

[21] Appl. No.: 729,053

[22] Filed: Jul. 12, 1991

[51] Int. Cl.⁵ .................................. G01N 33/569
[52] U.S. Cl. ................... 435/7.22; 435/7.9; 435/7.92; 435/7.93; 435/7.94; 435/947; 530/388.6
[58] Field of Search .......... 435/7.22, 7.9, 7.92, 435/7.93, 7.94, 975, 240.27; 436/543, 544; 530/388.6, 391.6

[56] References Cited

U.S. PATENT DOCUMENTS

4,376,110  8/1980  David et al. .................. 436/513
4,530,908  7/1985  Strand ............................. 435/7.22

FOREIGN PATENT DOCUMENTS

83/01837  5/1983  PCT Int'l Appl. ............... 435/7.22

OTHER PUBLICATIONS

Solano et al, Abstract 9, Proceedings of the American Association of Veterinary Parasitologists, 35th Annual Meeting, p. 23 (1990).
Espino et al, J. Clin. Microbiol., 28(12):2637-2640 (Dec. 1990).
Santiago et al, Chem. Abstracts, 106(5):380, Abstract No. 31089x (Feb. 2, 1987).
Zimmerman et al., "Diagnosis of Ovine Fascioliasis by a Dot Enzyme-Linked Immunosorbent Assay: A Rapid Microdiagnostic Technique," Am. J. Vet. Res., vol. 46, No. 7, pp. 1513-1515 (1985).
"Fasciola hepatica Antibody Test Kit," Disease Detection International (Sep. 1987).
Santiago, N., et al., "Isolation of Fasciola hepatica Genus-Specific Antigens." Internat. J. Parasitol., vol. 14 (2), pp. 197-206 (1984).
Hillyer, G. V., "Isolation of Fasciola heptaica tegument antigens," J. Clinic. Microbiol., pp. 695-699 (1980).
Irving, D. O., et al., "Characterization of Excretory-Secretory Antigens of Fasciola hepatics," Parasitol., vol. 85, pp. 179-187 (1982).
Santiago, N. et al., "Isolation of Potential Serodiagnostic Fasciola Hepatica Antigens by Electroelution from Polyacrylamid Gels," Am. J. Trop. Med. Hyg., vol. 35 (6), pp. 1210-1217 (1986).
Langley, R. J., et al., "Detection of Circulating Parasite Antigens in Murine Fascioliasis by Two-site Enzyme-linked Immunosorbent Assay," Am. J. Trop. Med. Hyg., vol. 41 (4), pp. 472-478 (1989).
Marrero, C. A., et al., "Evaluation of Immune-Diagnostic Antigens in the Excretory-Secretory Products of Fasciola hepatics," J. Parasitol., vol. 74 (4), pp. 646-652 (1988).
Santiago, N. et al., "Antibody Profiles by EITB and ELISA of Cattle and Sheep Infected with Fasciola hepatica," Parasitol., vol. 74 (5), pp. 810-818 (1988).
Stibbs, H. H., et al., "Enzyme Immunoassay for Detection of Giardia lamblia Cyst Antigens in Formalin-Fixed and Unfixed Human Stool," J. Clinic. Microbiol., vol. 26 (9), pp. 1665-1669 (1988).
Rosoff, J., et al., "Isolation and Identification of a Giardia lamblia-Specific Stool Antigen (GSA 65) Useful in Coprodiagnosis of Giardiasis," J. Clinic. Microbiol., vol. 23 (5), pp. 905-910 (1986).
Attallah et al., "Fast Dot-ELISA on Urine to Diagnose Shistosoma mansoni Infection," abstract from Am. Soc. Trop. Med. Hyg. 39th Ann. Mtg., New Orleans, p. 113 (Nov. 1990).
Teplukhin et al., "The Diagnostic Value of Erthrocytic Immunoreagents Used for the Detection of O. felineus Antigens" Meditsinskaia Parazitologiia I Parazitarnye Bolezni (Moscow), No. 5, Sep.-Oct. 1986, pp. 37-40 (English Abstract pp. 39-40).
Hasan, et al., "Bovine T-Cell Immunity to Fasciola hepatica Antigens," Abstract from the Proceedings of the American Association of Veterinary Parasitologists 35th Annual Meeting (Jul. 21-24, 1990).
Youssef, et al., "Diagnosis of Human Fascioliasis by the Counter-immunoelectrophoresis Using Specific Antibodies to Detect Copro-Antigens" (ASTMH Abstract 1989), abstract of poster presentation made in Honolulu, Hi. at the 38th Annual Meeting of the American Society of Tropical Medicine and Hygiene held Dec. 10-14, 1989.
Youssef et al., "Early Diagnosis of Human Fascioliasis by the Detection of Copro-antigens Using Counterimmunoelectrophoresis," Trans. Roy. Soc. Trop. Med. & Hyg., vol. 85, pp. 383-384 (1991).
Deplazes et al., "An Enzyme-Linked Immunosorbent Assay for Diagnostic Detection of Taenia saginata Copro-antigens in Humans," Trans. Roy. Soc. Trop. Med. & Hyg., vol. 85, pp. 391-396 (1991).

*Primary Examiner*—Esther L. Kepplinger
*Assistant Examiner*—Carol E. Bidwell
*Attorney, Agent, or Firm*—John H. Runnels

[57] ABSTRACT

A stable antigen useful in the detection of Fasciola hepatica (or liver fluke) infections is disclosed. The antigen may be found in feces, bile, and intestinal contents. Monoclonal antibodies useful in detecting the antigen are disclosed. The method of this invention facilitates the detection of current Fasciola hepatica infections.

12 Claims, 10 Drawing Sheets

--- Infected Feces vs. Rabbit Anti-Fresh Fluke Antigen

— Infected Feces vs. Rabbit Normal Preinoculation Serum

--- Infected Feces vs. Rabbit Anti-Fresh Fluke Antigen

___ Infected Feces vs. Rabbit Normal Preinoculation Serum

--- Infected Feces vs. Rabbit Anti-Fresh Fluke Antigen

— Infected Feces vs. Rabbit Normal Preinoculation Serum

--- Infected Feces vs. Rabbit Anti-Fresh Fluke Antigen

___ Infected Feces vs. Rabbit Normal Preinoculation Serum

--- Infected Feces vs. Rabbit Anti-Fresh Fluke Antigen

___ Infected Feces vs. Rabbit Normal Preinoculation Serum

-.- Uninfected Feces vs. Rabbit Anti-Fresh Fluke Antigen

--- Infected vs. Positive Cattle Serum

___ Infected vs. Normal Cattle Serum

--- Infected vs. Positive Cattle Serum

— Infected vs. Normal Cattle Serum

--- Infected vs. Positive Cattle Serum

— Infected vs. Normal Cattle Serum

--- Infected vs. Positive Cattle Serum

___ Infected vs. Normal Cattle Serum

--- Infected vs. Positive Cattle Serum

___ Infected vs. Normal Cattle Serum

-.- Uninfected vs. Positive Cattle Serum

DIAGNOSIS OF FASCIOLA INFECTIONS BY DETECTION OF ANTIGENS IN FECES OR INTESTINAL CONTENT

This invention pertains to the diagnosis of *Fasciola hepatica* (liver fluke) infections, particularly to the diagnosis of such infections through the detection of antigens in the feces or bile of infected animals.

Liver fluke infection, or fascioliasis, is a serious disease of cattle, sheep, goats, buffalo, and other ruminants. It can be an incidental parasite in other animals, and also can infect man, causing an important public health problem in some countries. About five percent of cattle in the United States are infected, and the comparable percentages in some countries are higher, reaching twenty to forty percent, for example, in Egypt. The disease is debilitating, decreasing production of milk, meat, and wool, and results in losses due to condemned livers when the affected animals are slaughtered. In addition, it can lead to chronic low-grade anemia, and emaciated carcasses at slaughter.

In the United States, fascioliasis occurs primarily in Gulf Coast states and in western states in regions where suitable soil type and sufficient moisture support populations of lymnaeid (snail) intermediate hosts Following the Food and Drug Administration's 1979 removal of hexachlorethane from the market, losses from fascioliasis were considered important enough for fourteen states to apply for emergency authorization to use the drug albendazole in cattle and sheep. These states accounted for 40% of the United States cattle population, and 60% of its sheep population in 1980.

In cattle, the liver flukes *Fasciola hepatica* and *Fascioloides magna* are responsible for the condemnation at slaughter/inspection of 1 to 1.5 million livers annually. This number represents 20 to 25% of livers condemned each year, or livers from 3 to 4% of all cattle slaughtered. Assuming an average value of $5/liver, the annual direct loss is at least $5 million. In addition to these quantifiable direct losses, reports increasingly indicate that indirect losses due to fascioliasis may be even greater. Indirect losses include reduction in average daily body weight gain and lower feed conversion ratios in the feedlot, reduced milk production in dairy cattle, and reduced herd performance in cow-calf operations. Significant production losses may occur in cattle herds with a rate of infection greater than 25%. The rate of weight gain in feeder calves may be reduced by 8 to 28% in animals infected with 40 to 140 *F. hepatica* flukes per animal. These moderate to severe infect[on rates are commonly encountered in cattle in enzootic areas. In 1973, losses were estimated at $30 million annually due to liver condemnations and production losses, assuming a total of 5 million infected cattle. There is evidence that the prevalence of *F. hepatica* is increasing in the United States, particularly in western states where irrigated pastures are increasingly used.

In sheep, *F. hepatica* is more pathogenic than in cattle, and infection is often associated with anemia, poor reproduction, and death. In goats, *F. hepatica* is also highly pathogenic, and mortality rates are high.

Focal sedimentation procedures, with microscopic examination for eggs, are the standard means of diagnosing *F. hepatica* infection in cattle. Problems associated with these methods include the following: (1) They are time consuming, requiring 15 to 30 minutes per sample. (2) The examination of 10 to 15 samples is typically required to evaluate a herd or feedlot group effectively. (3) Egg counts are low, commonly fewer than 5 eggs per gram, even in heavily infected herds. (4) Herd egg counts vary widely among animals because parasites are usually not uniformly dispersed. Most flukes and eggs shed may come from a few highly susceptible animals. (5) Herd egg counts peak and wane depending on seasonal transmission. (6) Immature fluke infections are not detected. (7) The use of different techniques makes it difficult to compare results from different laboratories.

There are also serologic tests for the detection of circulating antibodies. Existing tests are limited by low sensitivity and specificity, and by the difficulty of distinguishing current infections from prior infections in cows exposed over several years. A need exists for a means of rapid diagnosis which detects only current fluke burdens. See Zimmerman et al., "Diagnosis of Ovine Fascioliasis by a Dot Enzyme-Linked Immunosorbent Assay: A Rapid Microdiagnostic Technique," Am. J. Vet. Res., Vol. 46, No. 7, pp 1513–15 (1985), which describes a serologic diagnostic technique. See also the product information sheet for a serologic test kit, "Fasciola hepatica Antibody Test Kit," Disease Detection International (Sept. 1987).

Diagnosis of fascioliasis using serological methods permits a more accurate identification of infected animals at all stages of infection than do the prior parasitologic methods that depend on finding eggs in feces. For examples of such serological methods, see Santiago, N., "Isolation of *Fasciola hepatica* Genus-Specific Antigens." Internat. J. Parasitol., Vol. 14 (2), pp. 197–206 (1984); Hillyer, G. V., "Isolation of Fasciola hepatica tegument antigens," J. Clinic. Microbiol., pp. 695–699 ( 1980 ); Irving, D. O., et al., "Characterization of Excretory-Secretory Antigens of *Fasciola hepatica*" Parasitol Vol 85, pp 179–188 (1982), Santiago, N., et al., "Isolation of Potential Serodiagnostic *Fasciola Hepatica* Antigens by Electroelution from Polyacrylamide Gels," Am. J. Trop. Med. Hyg., Vol. 35 (6), pp. 1210–1217 (1986); Langley, R. J., et al., "Detection of Circulating Parasite Antigens in Murine Fascioliasis by Two-site Enzyme-linked Immunosorbent Assay," Am. J. Trop. Med. Hyg., Vol. 41 (4), pp. 472–478 (1989); and Marrero, C. A., et al., "Evaluation of Immune-Diagnostic Antigens in the Excretory-Secretory Products of *Fasciola hepatica*," J. Parasitol., Vol. 74 (4), pp. 646–652 (1988)

The sensitivity and specificity of serological tests are affected by the antigens used, cross reactivity with other parasites, and the relative number and stage of development of fluke burdens. Furthermore, a serological test based on antibody detection may be positive when there is no longer an active infection, because the antibody (IgG) half-life in blood is about twenty-one days.

Irving, D. O., et al., "Characterization of Excretory-Secretory Antigens of *Fasciola hepatica*," parasitol., Vol. 85, pp. 179–188 (1982); santiago, N., et al., "Isolation of Potential Serodiagnostic *Fasciola hepatica*Antigens by Electroelution from Polyacrylamide Gels," Am. J. Trop Med. Hyg., Vol. 35(6), pp 1210–1217 (1986), Marrero, C. A., et al., "Evaluation of Immune-Diagnostic Antigens in the Excretory-Secretory Products of *Fasciola hepatica*," J. Parasitol., Vol. 75 (4), pp. 646–652 (1988); and Santiago, N., et al., "Antibody Profiles by EITB and ELISA of Cattle and Sheep Infected with *Fasciola hepatica*," J Parasitol Vol 74 (5), pp. 810–818

(1988) have reported detecting proteins from in vitro-derived excretory-secretory product from the fluke at 23 kD, 24kD and 26kD, 23–28 kD, 25–30 kD, and 20–28 kD, respectively. Santiago, N., et al., "Isolation of Fasciola hepatica Genus-Specific Antigens," Internat. J. Parasitol., Vol. 14 (2), pp. 197–206 (1984) reported isolating *F. hepatica*-specific antigens from fluke tegument extract, and reported serological diagnostic antigens at a molecular weight range of 14–43 kD.

Attallah et. al., "Fast Dot-ELISA on Urine to Diagnose *Schistosoma mansoni* Infection," abstract from Am. Sec. Trop Med. Hyg. 39th Ann. Mtg., New Orleans, p. 113 (November 1990), which is not admitted to be prior art, mentions a murine monoclonal antibody to *Schistosoma mansoni* worms used to develop a fast dot-ELISA prototype assay to detect *S. mansoni* antigen(s) in urine.

Teplukhin et al., "The Diagnostic Value of Erythrocytic Immunereagents Used for the Detection of *O. felineus* Antigens," Meditsinskaia Parazitologiia I Parazitarnye Bolezni (Moscow), No. 5, Sept.-Oct. 1986, pp. 37–40 (English Abstract pp. 39–40), discusses the diagnosis of opisthorchiasis through passive hemagglutination and antibody neutralization tests for the detection of *O. felineus* antigens in feces.

Stibbs, H. I., et al., "Enzyme Immunoassay for Detection of Giardia lamblia Cyst Antigens in Formalin-Fixed and Unfixed Human Stool," J. Clinic. Microbiol., Vol. 26 (9), pp. 1665–1669 (1988), describes a method for diagnosing *Giardia lamblia* infection in humans by detection of a specific parasite antigen in the stool by an enzyme immunoassay. Giardia is a protozoan that replicates in very large numbers in the gut, producing stable antigen that survives the digestive process in sufficient quantities for detection. See also Rosoff, J., et al., "Isolation and Identification of a *Giardia lamblia*-Specific Stool Antigen (GSA 65) Useful in Coprodiagnosis of Giardiasis," J. Clinic. Microbiol., Vol. 23 (5), pp. 905–910 (1986).

*Fasciola hepatica*, however, does not replicate in the gut, and exists in the liver and biliary system only in small numbers.

In the present invention, diagnostically useful antigens in bile and faces from *F. hepatica*-infected cattle have been discovered, and have been characterized by sodium dodecylsulfate-polyacrylamide gel electrophoresis (SDS-PAGE), by enzyme-linked immunotransfer blot (EITB) techniques, and by enzyme-linked immunosorbent assay (ELISA).

Diagnosis of parasites by the present invention, through detection of specific, stable antigens in faces of the infected animals, offers several advantages over diagnosis by serologic methods based on antibody detection. Faces are often more readily accessible than serum samples. Antigan detection methods detect current or recent infections, rather than historical exposures, as serological methods may. Groups of animals can be screened for infection, without time-consuming microscopic fecal examination procedures that vary in accuracy with stage of parasite development. Faces-derived antigen is stable for months at 4° C. Worm numbers can be estimated from the amount of antigen present in faces. Fecal antigan detection methods can be adapted for use in all *F. hepatica*-susceptible species, including cattle, sheep, goats, and humans. Antigan may be detected using monoclonal antibody techniques. Monoclonal antibodies have been developed to the 26 kD antigen Gellah 26.

Figure 1A:
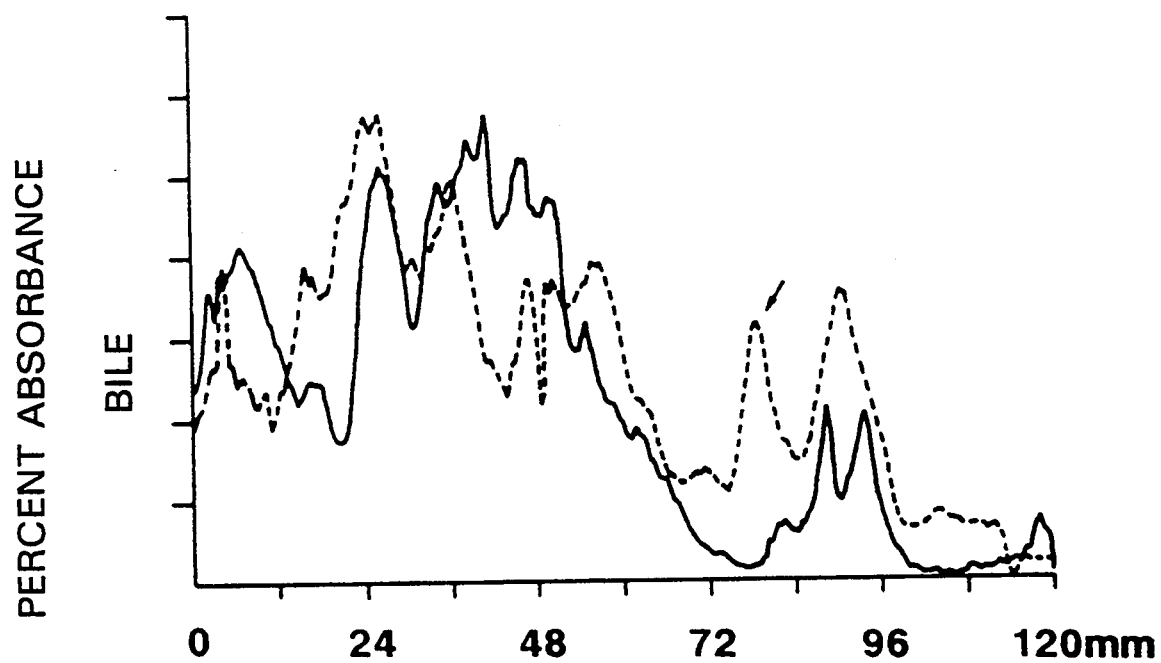
FIG. 1A–1E illustrate densitometer scan plots of EITB strips after reaction of samples with rabbit anti-FFA serum.

Antigens. Samples of whole bile, faces, and contents of the duodenum, jejunum, and colon from both *F. hepatica*-infected (three calves) and uninfected (five calves) cattle were collected from slaughterhouse near Baton Rouge, Louisiana; and from 20 infected calves for which fluke burdens had previously been determined as part of an unrelated pharmaceutical test with Netobimin (Schering Corporation). For the latter, eleven Netobimin-treated and nine untreated calves were slaughtered and examined twenty-one days after the drug treatment.

Five ml of whole bile from each sample were dialyzed separately in 6000–8000 molecular weight (MW) cut-off dialysis tubes overnight at 4° C, in two changes of saline solution. Samples were then concentrated at room temperature to 1/5 of original volume by absorption against polyvinyl pyrrolidone (360,000 MW). The samples were stored at −20° C. until used.

For feces and intestinal contents, 5 gram samples were mixed separately in an equal amount of distilled water, and sonicated for 5 minutes under 150. Watt interrupted pulse output at 50% power cycle using a Sonifier cell disrupter (Model W 350). The power of sonication should preferably be neither too high nor too low. The supernatant was separated by centrifugation (3000 rpm for 15 minutes), dialyzed, concentrated, and preserved as described above for bile.

F. hepatica fresh antigen (FFA) was prepared by the method of Farrell, C. J., et al., "An Enzyme-Linked Immunosorbent Assay for Diagnosis of *Fasciola hepatica* Infection in Cattle," Am. J. Vet. Res., Vol. 42 (2), pp. 237–240 (1981), which is incorporated by reference. Fresh collected flukes were washed for 30 minutes in phosphate-buffered saline (PBS) (pH 7.4), mixed with the same buffer at 1 ml/gram of fluke, ground in a mortar, and then homogenized at 4° C. to obtain a uniform suspension. This material was held at 4° C. for 24 hours, and then centrifuged at 12,000 g for 30 minutes at 4° C. The supernatant was separated, and the protein content of the supernatant was determined by the Bicinchoninic acid assay method (Pierce Chemical Co., Rockford, Ill.).

*F. hepatica* eggs were sieved (with a Flukefinder ®, Pullman, Washington) from tap-water-diluted bile, sedimented from the infected bile, washed in distilled water, and stored at 4° C. in aliquots with known numbers of eggs/ml of water.

Sera. Rabbit sera used for studies were: (1) anti-FFA (two rabbits), (2) anti-*F. hepatica* egg (two rabbits), and (3) negative preinoculation sera (four rabbits). Cattle sera used were: (1) *F. hepatica*-infected (three calves selected for high titers using ELISA), (2) negative controls, and (3) *Fascioloides magna*-infected (separate sara obtained from W. J. Foreyt, Pullman, Washington and B. E. Stromberg, Minneapolis, Minn.).

Rabbit hyper-immune sera were raised against whole *F. hepatica* eggs or FFA. Four 2-month-old white New Zealand rabbits were bled for negative control sara, and then injected with either 1.2 mg FFA protein or one million eggs, mixed in an equal volume of Freund's complete adjuvant, subcutaneously at different places in the back of the rabbit. After 3 weeks, 3 consecutive injections of 0.4 mg protein FFA, or of 330,000 eggs, each in equal volumes of Freund's incomplete adjuvant, were given intramuscularly at biweekly intervals. Rabbits were bled from the ear vein for serum collection 10–14 days after the last injection. The collected sara were stored at −20° C. until used.

SDS-PAGE. 500 ul (microliter) from each sample was solubilized separately in an equal amount of sample buffer (0.0625 M tris hydrochloride (PH 6.8), 2% sodium dodecylsulfate (SDS), 10% glycerol, 5% beta-mercaptoethanol, 0.002% Bromophenol blue), and heated for 10 minutes at 100° C. Proteins were electrophoresed, using the method of Laemmli, U. K., "Cleavage of Structural Proteins During Assembly of the Head of Bacteriophage T4," Nature, Vol. 227, pp. 680–685 (1970), which is incorporated by reference. The SDS-PAGE gel was prepared using 1 mm thick, two-well combs. The small well was loaded with 10 ul of Bethesda Research Laboratories, Inc. (Grand Island, NY) low MW protein marker (Mr). The large well was loaded with 800 ul of the sample mixture. The stacking gel contained 4% monomer, and the separating gel contained 12% monomer. Electrophoresis was carried out through the 1 mm thick stacking and separating gel at 3–4 watts/gel for 4–5 hours at 4° C.

Protein blot analysis was performed according to the method of Towbin, H. et al., "Electrophoretic Transfer of Proteins from Polyacrylamide Gels to Nitrocellulose Sheets: Procedure and Some Application," Proc. Nat. Acad. Sci. USA, Vol. 7b, pp. 4350–4354 (1979), which is incorporated by reference. Proteins separated by SDS-PAGE were transferred onto nitrocellulose (NC) membranes in transfer buffer (0.242% tris-base, 1.126% glycine, and 20% methanol) in an electrophoretic transfer cell (Transblot, BIO-RAD Laboratories, Richmond, Calif.) overnight at 4° C., using low field intensity (100 mA, 30 V). After transfers were completed, the NC membranes were dried in a partial vacuum at 60° C.

The EITB was done as described by Tsang et al., "Enzyme-Linked Immunotransfer Blot Technique (EITB) for Studying the Specificities of Antigens and Antibodies Separated by Gel Electrophoresis," Meth. Enzymology, Vol. 92, pp. 377–91 (1983); and Santiago, N., et al., "Isolation of Potential Serodiagnostic Fasciola hepatica Antigens by Electroelution from Polyacrylamide Gels," Am. J. Trop. Med. Hyg., Vol. 35 (6), pp. 1210–1217 (1986), which are both incorporated by reference. All sera were tested at 1:100 dilution. Goat anti-bovine and goat anti-rabbit IgG affinity purified peroxidase-labeled conjugates were used at 1:1000 dilution, Optical densities of different bands on selected NC strips were measured using a Joyce-Loebl Densitometer.

EXAMPLES

Preliminary SDS-PAGE examinations were done on 23 naturally infected calves with known numbers of F. hepatica and Paramphistomum eggs per 2 grams of feces (EP2G); 9 of these calves had known F. hepatica numbers recovered from the liver at necropsy, Five additional calves served as uninfected controls. Ten representative infected animals were selected for further study by EITB, along with the five uninfected controls, based on egg counts, worm burdens, and history. Fluke egg counts in the ten infected calves varied from 1 to 155 EP2G F. hepatica and 0 to 47 EP2G Paramphistomum. Adult F. hepatica worm burdens in six of the ten calves examined at necropsy ranged from 14 to 663.

Table 1 shows the fluke infection history, and detection by EITB of the 26 kD Mr. band in bile, faces, duodenal content, jejunal content, and colon content of these ten infected and five uninfected calves. Rabbit anti-FFA and F. hepatica-infected cattle sara consistently reacted positively. Rabbit anti-egg, negative rabbit, F. magna-infected cattle, and negative cattle sara reacted negatively or in consistently.

TABLE 1

Detection of the 26 KD band by enzyme linked immunotransfer blots prepared from dialyzed, concentration samples of bile, feces, duodenal content, jejunal content and colon content of 10 F. hepatica infected and 5 uninfected control cattle.

| Animal No. | Fluke Infection History | | | $R_x$ | Bile | | Feces | | Duodenal contents | | Jejunal contents | | Colon Contents | |
|---|---|---|---|---|---|---|---|---|---|---|---|---|---|---|
| | EP2G | | No. | | Rabbit | Cattle | Rabbit | Cattle | Rabbit | Cattle | Rabbit | Cattle | Rabbit | Cattle |
| | F. hep | Para | F. hep | | 1 2 3 | 4 5 6 | 1 2 3 | 4 5 6 | 1 2 3 | 4 5 6 | 1 2 3 | 4 5 6 | 1 2 3 | 4 5 6 |
| A | 5 | 1 | (5) | $R_x$ | + − | + − | | + | | | | | + | + − − |
| B | 8 | 0 | 84 | − | + − − | − | | + | | | | | | |
| C | 11 | 1 | (3) | − | + − − | + − − | | + − − | + + − | + − − | + + − | + − − | + − | + − − |
| D | 102 | 3 | 1 | $R_x$ | + − − | + − − | | + − − | + + − | + − − | + − − | + − − | + − | + − − |
| E | 6 | 4 | 14 | − | − | + − | | + − − | + + − | + − − | + − − | + − − | + − | |
| F | 155 | 47 | 663 | − | | − − | − − | + − − | + − | + − − | + − − | + − − | + − | |
| I | 1 | 3 | (1) | $R_x$ | | | | | | | | | + | + − − |
| O | ND | ND | 149 | − | | | + − − | + − | | | | | | |
| P | ND | ND | 37 | − | | | + − − | + − | | | | | | |
| Q | ND | ND | 49 | − | | | + − − | | | | | | | |
| G | Negative control | | | | − | | | | | | | | | |
| H | Negative control | | | | − | | | | | | | | | |
| L | Negative control | | | | − | | | | | | | | | − |
| M | Negative control | | | | − | | | | | | | | | − |
| N | Negative control | | | | | | | | | | | | | − |

* 1-Rabbit hyper-immune sera against FFA, 2-Rabbit hyper-immune sera against whole F. hepatica eggs, 3-Negative rabbit sera, 4-F. hepatica infected cattle sera, 5-F. magna infected cattle sera and 6-Negative cattle sera.
+ Number of mature and (immature) flukes recovered at necropsy in cattle treated and untreated with flukecide.
( ) Immature flukes EITB against proteins transferred to NC membranes revealed reaction by one or more of the six sara to five main band groups located between the protein molecular weight standards at 104–66 kD Mr., 66–42 kD Mr., 42–2.5 kD Mr., 25–18 kD Mr., and directly above 25 kD Mr. The first four band groups reacted against sara from rabbits and cattle exposed to F. hepatica antigen, but also reacted non-specifically with the negative rabbit, cattle control, and F. magna-infected sara.

A band detected by EITB in the area corresponding to 26 kD Mr. was thought best for diagnostic test development. The antigen, named Gellah 26, appeared to be stable, and could be detected in fecal samples stored at 4° C. for one month. This band reacted strongly with both rabbit anti-FFA and infected cattle sara. It reacted weakly with rabbit anti-egg in duodenal content only, and had no reaction with negative rabbit or *F. magna*-positive cattle sara. With negative cattle serum, weak reaction was noted for animal "E" in duodenum content and for animal "D" in feces. This 26 kD band was not detected by Coomassie blue stain in SDS-PAGE gels, or by ponceau-S (0.5%) stained NC strips. Initial EITB results on 10 *F. hepatica*-infected calves revealed variable color densities to rabbit anti-FFA and *F. hepatica* cattle sera by visual observation at the 26 kD band position.

Figure 1B:
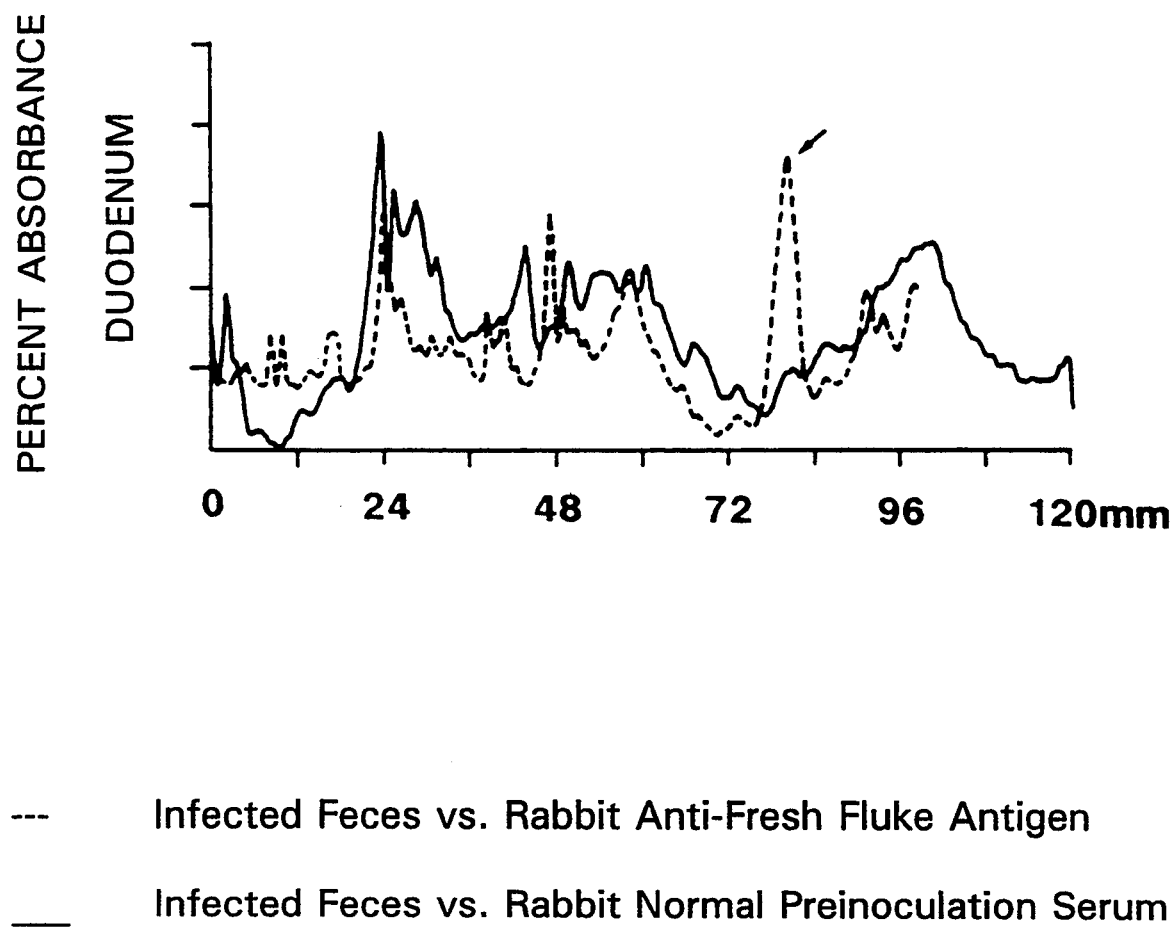
Figure 1C:
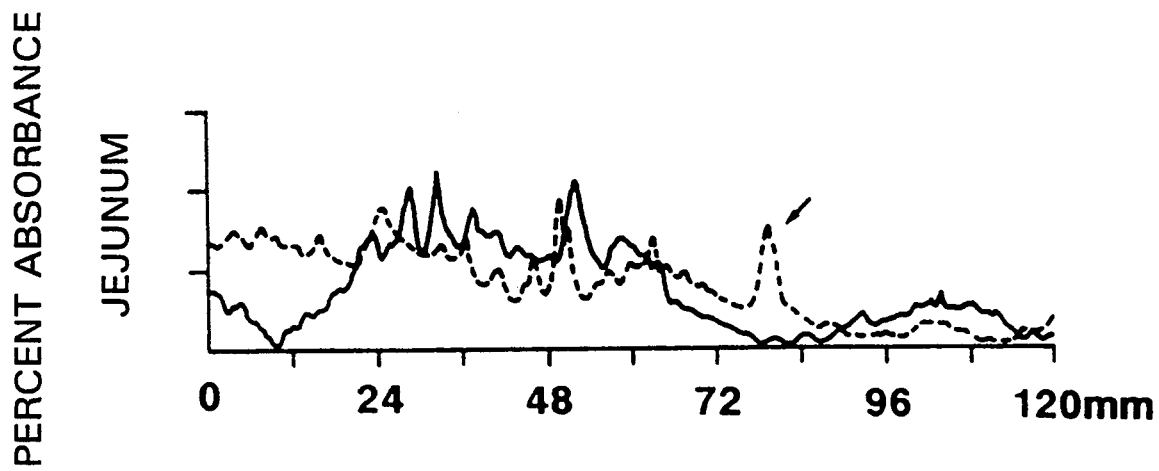
Figure 1D:
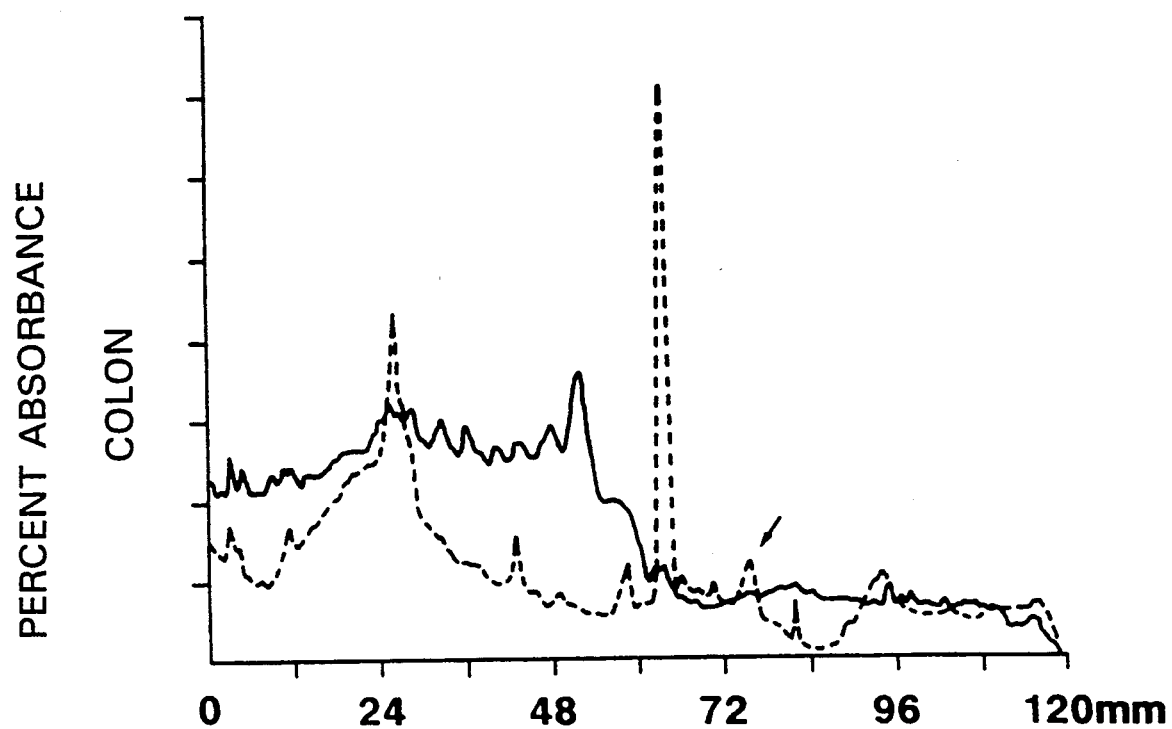
Figure 1E:
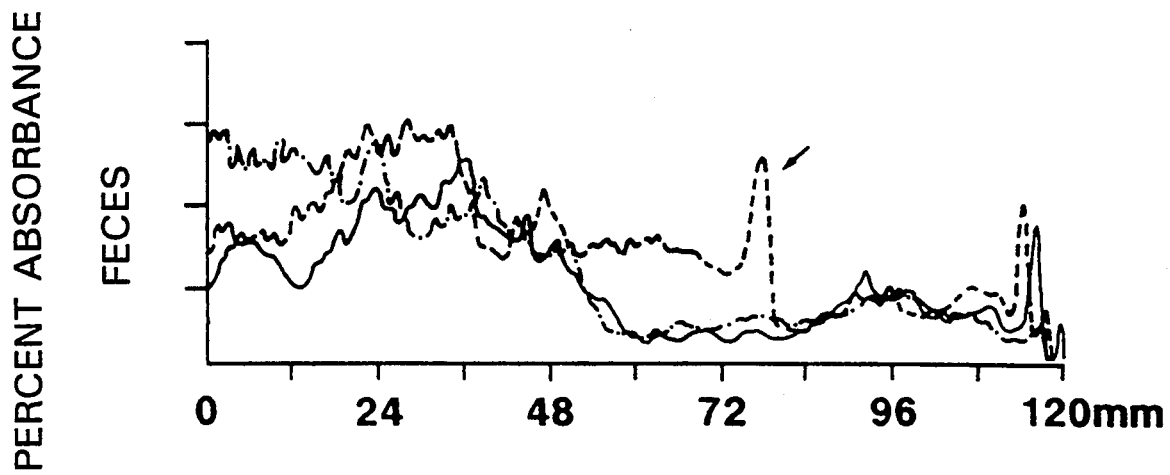
Figure 2A:
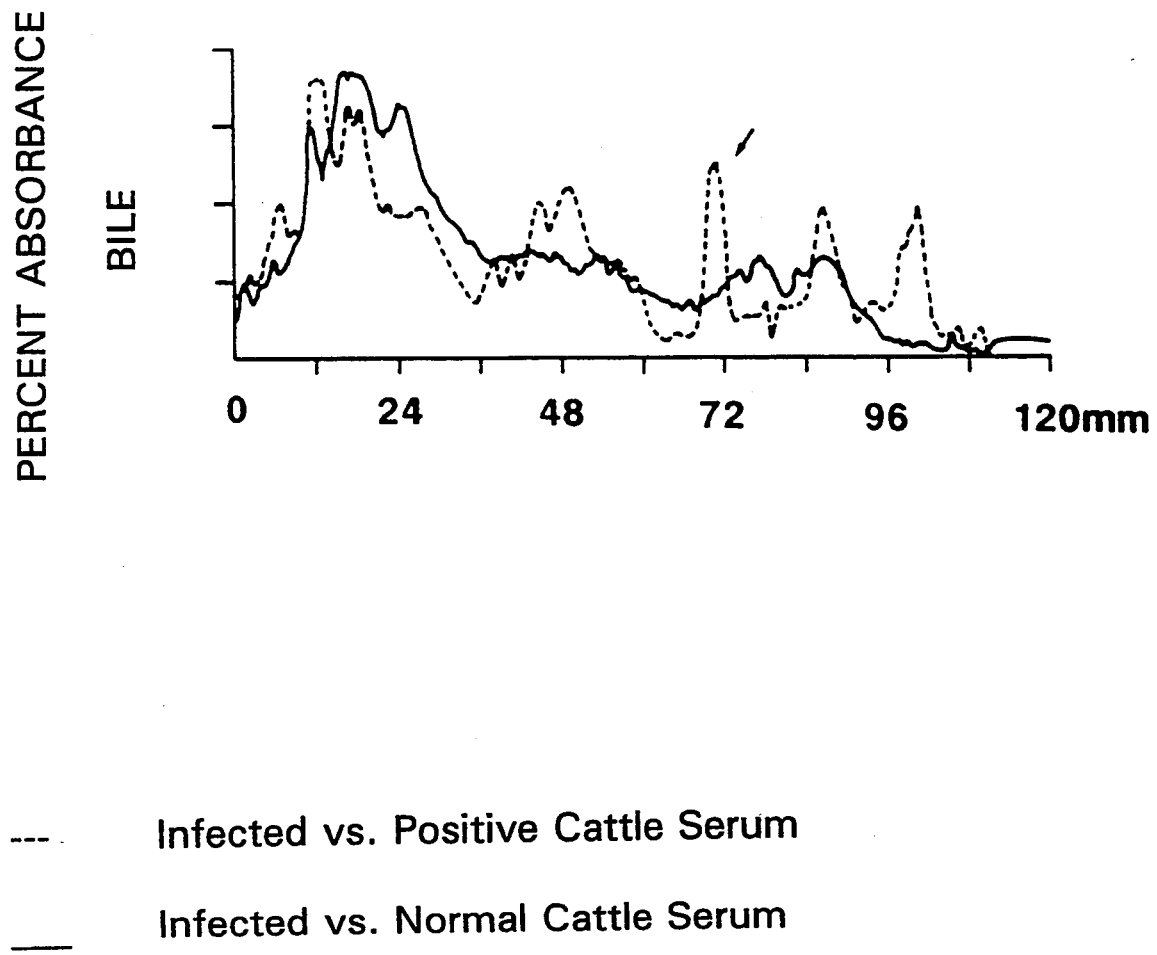
FIG. 2A–2E illustrate densitometer scan plots of EITB strips after reaction of samples with *F. hepatica*-positive cattle serum.
Figure 2B:
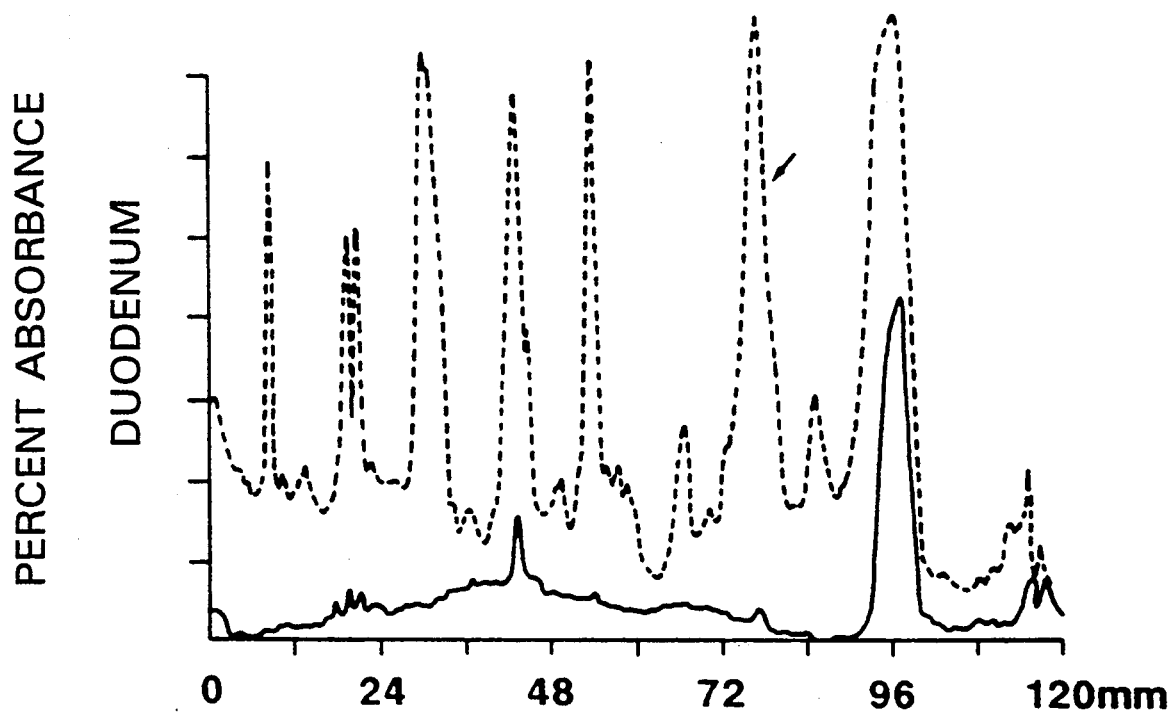
Figure 2C:
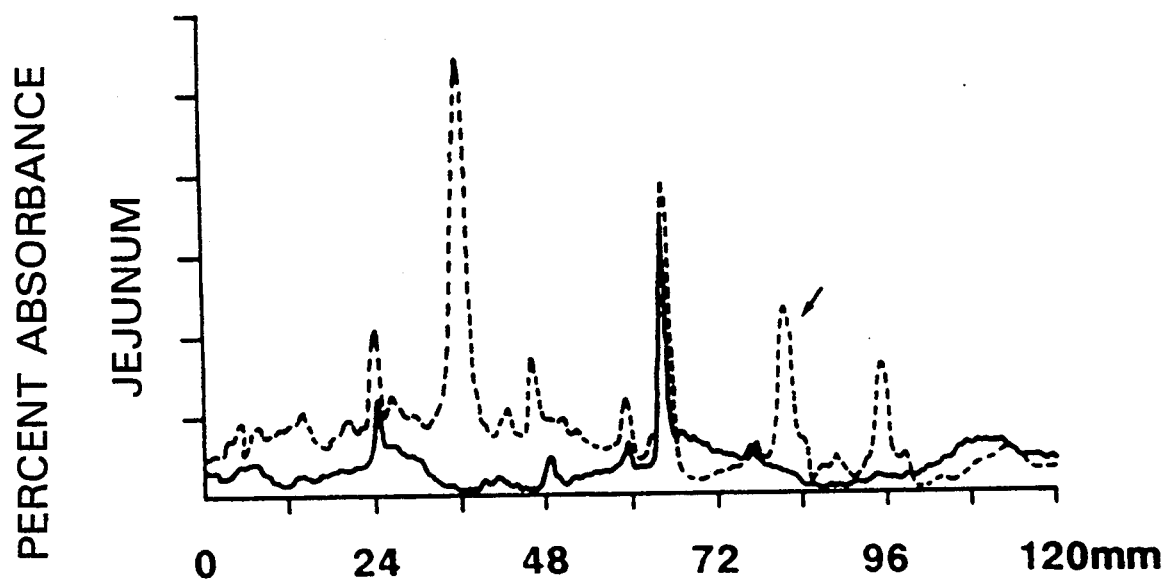
Figure 2D:
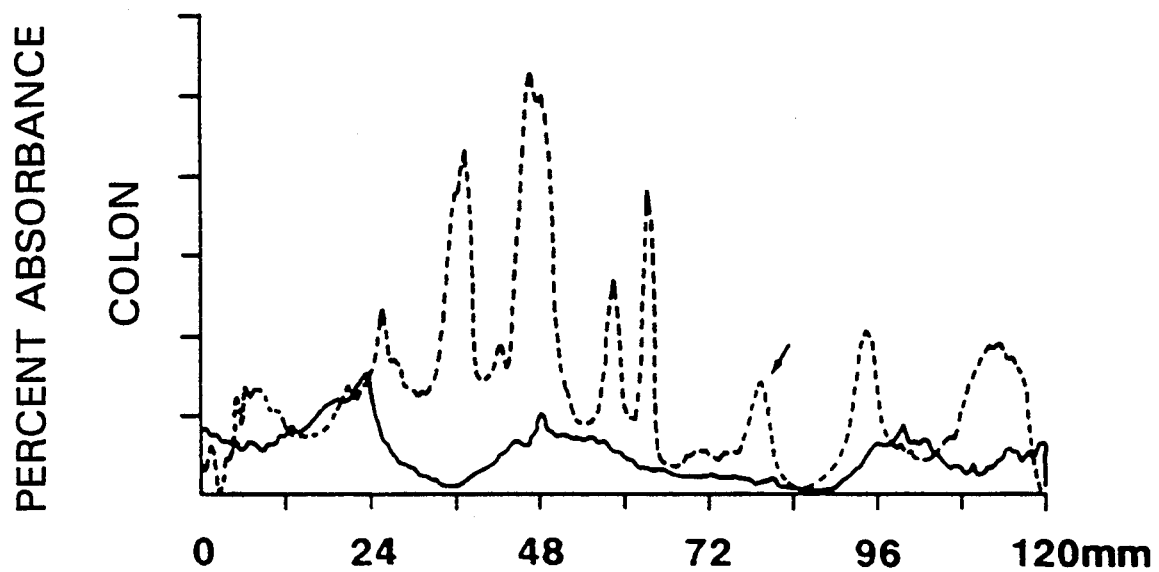
Figure 2E:
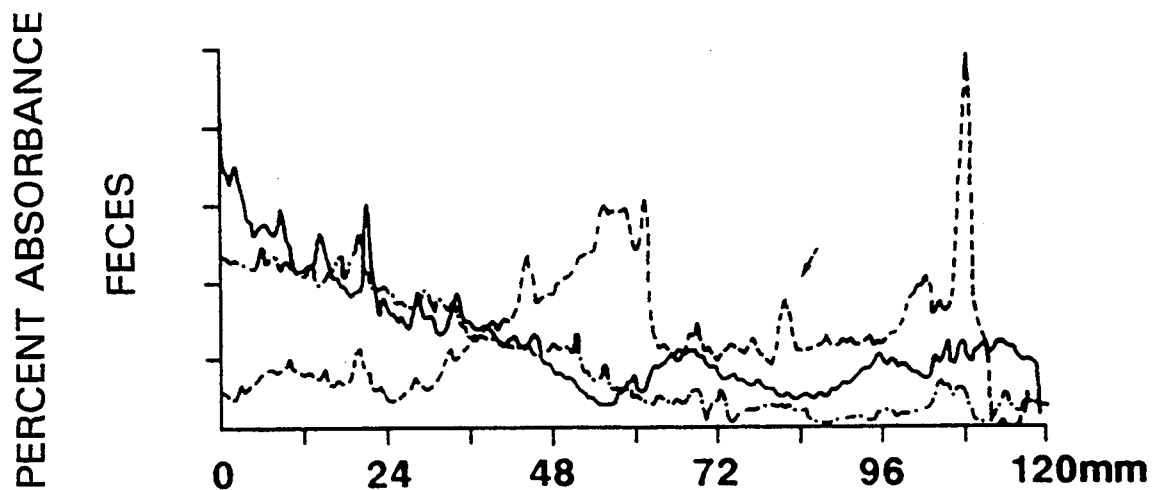

Densitometer scans of selected positive EITB strips clearly demonstrated the above pattern of positive and negative reactions. The results for animal "C" are shown in FIGS. 1A–1E and 2A–2E; except that results for animal "O" are shown for feces versus rabbit anti-FFA and rabbit control sera. (For animal C, overdevelopment of color occurred, and the 26 kD band was therefore missed.) FIGS. 1A–1E and 2A–2E illustrate densitometer scan plots of EITB strips showing the 26 kD band (indicated by arrows) in bile, duodenal contents, jejunal contents, colon contents, and feces, after reaction with rabbit anti-FFA serum (FIG. 1A–1E respectively) or *F. hepatica*-positive cattle serum (FIG. 2A–2E respectively).

Table 2 shows the EITB reactions of six sera to 104–66 kD, 66–42 kD, 42–25 kD, 26 kD, and 25–18 kD band ranges for bile, duodenal, jejunal, colon, and fecal samples from ten cattle infected with *F. hepatica*. The 26 kD band reacted strongly with rabbit anti-FFA and *F. hepatica*-infected cattle sera. There was weak reactivity to rabbit anti-egg sera in duodenal content only. No reaction was observed for negative rabbit or *F. magna*-infected cattle. For negative cattle sera, there was a weak reaction for animal E in duodenal content and for animal D in feces; inconsistent or nonspecific reactivity was observed for other band ranges.

The group of bands between 104 and 66 kD Mr. reacted specifically with rabbit anti-FFA, rabbit anti-egg, and, except for jejunal content, *F. hepatica* infected cattle sera. Inconsistent band react ions occurred with negative rabbit, *F. magna*-infected cattle, negative rabbit, and negative cattle sera.

Bands that occurred between 66 and 42 kD Mr. reacted specifically with rabbit anti-FFA, rabbit anti-egg, negative rabbit, and *F. hepatica*-infected cattle sera. Negative cattle serum reacted with all strips, except for colon content and some feces samples. *F. magna* cattle sera detected this band in some of the bile and duodenal samples.

The area between 42 and 25 kD Mr. contained several bands that reacted with rabbit anti-FFA and rabbit anti-egg. *F. hepatica*-infected sera reacted with some bands in all samples, except for feces and some duodenal contents. Negative rabbit serum did not react with this band group except in jejunal contents and some duodenum samples. *F. magna*-infected and negative cattle sera reacted with some of these bands, but only in bile and duodenal contents.

Bands present between 25 and 18 kD Mr. reacted with rabbit anti-FFA serum and, except in feces and some of the duodenal contents, with *F. hepatica*-infected sera. Rabbit anti-egg serum detected bands in bile and duodenal contents only. Negative cattle serum did not react with colon, feces, or some duodenal and jejunal contents. Negative rabbit serum and *F. magna*-infected sera did not detect these bands, except for a few duodenal contents samples.

The Gellah 26 band, directly above 25 kD Mr., was present in feces, bile, and intestinal content samples, and reacted specifically with sera from five cattle infected by *F. hepatica*, and with rabbit anti-FFA hyper-immune sera. It did not react with negative cattle serum, negative rabbit serum, rabbit anti-*F. hepatica* whole egg serum, or with *F. magna*-infected cattle serum. The amount of Gellah 26 antigen, as determined by absorption with a densitometer, was highest in bile and duodenum samples, lower in jejunum and colon samples (possibly because of the watery nature of their contents), and then increased to greater levels in faces. The results suggest that the Gellah 26 antigan is not related to the

TABLE 2

Immunoblot reaction at various Molecular weight ranges against sera from rabbits hyperimmunized against *Fasciola hepatica* antigens and cattle infected with *Fasciola hepatica* or *Fascioloides magna*

| | 104–66 KD | | | | | | 66–42 KD | | | | | | 42–26 KD | | | | | | 26–25 KD | | | | | | 25–18 KD | | | | | |
|---|---|---|---|---|---|---|---|---|---|---|---|---|---|---|---|---|---|---|---|---|---|---|---|---|---|---|---|---|---|---|
| | Rabbit | | | Cattle | | | Rabbit | | | Cattle | | | Rabbit | | | Cattle | | | Rabbit | | | Cattle | | | Rabbit | | | Cattle | | |
| Sera | 1 | 2 | 3 | 4 | 5 | 6 | 1 | 2 | 3 | 4 | 5 | 6 | 1 | 2 | 3 | 4 | 5 | 6 | 1 | 2 | 3 | 4 | 5 | 6 | 1 | 2 | 3 | 4 | 5 | 6 |
| Bile | + | + | ± | + | ± | + | ± | + | + | + | ± | + | + | + | − | + | ± | + | + | − | − | + | − | − | + | + | − | + | − | + |
| Duodenal contents | + | + | ± | + | + | + | + | + | − | + | ± | + | + | + | ± | ± | ± | ± | + | + | − | + | − | − | + | + | ± | ± | ± | ± |
| Jejunal contents | + | + | ± | − | − | − | + | + | − | + | − | + | + | + | + | + | − | − | + | − | − | + | − | − | + | − | − | + | − | ± |
| Colon contents | + | | − | + | ± | − | + | | | ± | + | − | − | + | | | − | + | − | − | + | | | − | + | − | − | + | | |
| Feces | + | + | + | ± | ± | − | + | + | + | + | + | − | ± | + | ± | + | + | − | ± | + | − | + | + | − | − | + | − | − | − | − |

1- Rabbit hyper immune sera against FFA,
2- Rabbit hyper-immune sera against *F. hepatica* whole eggs,
3- Negative rabbit sera.,
4- *F. hepatica* infected cattle sera.,
5- *F. magna* infected cattle sera. and
6- Negative cattle sera.

worm eggs, because it did not react specifically with rabbit anti-egg sara by EITB. Without wishing to be bound by this theory, it is hypothesized that Gellah 26 protein may consist of stable components of excretory-secretory products, and/or tegument related antigan associated with physiological activities of the worms.

Two mice primed by the excretory-secretory products of liver flukes, and boosted by the protein band at 25–26 kD, produced highly specific anti-sera that detected only that band by EITB, without cross reaction with bands in any of the other four MW ranges reported above. Using the indirect ELISA method, the same mouse anti-sara were able to recognize antigan in fecal supernates from infected cattle, whereas serum from a non- immunized mouse did not; this was shown in a concentration-dependent manner for both fecal supernate (1:1, 1:10, 1:100) and mouse anti-sera (1:80, 1:120, 1:240).

Hybridoma cultures were prepared by fusing mouse myeloma cells with splenic lymphocytes from Balb/c mice that had been immunized against *F. hepatica* excretory-secretory product, and boosted via the intraperitoneal route with 25–26 kD fecal antigen protein on NC blots. Antibody in supernatants of six hybridoma cultures reacted with FFA preparations of both *F. hepgtic* and Paramphistomum by the indirect ELISA method. The reactivity with the Paramphistomum preparation was noticeably weaker.

Four of the six hybridoma wells producing positive antibody were cloned by limiting dilution according to the protocols described in Mishell and Shiigi, "Selected Methods in Cellular Immunology" (1980), which is incorporated by reference. Supernates containing monoclonal antibodies from the clones were collected and tested by ELISA against fresh fluke antigen of *F. hepatica* and Paramphistomum. Four monoclonal antibodies were found to recognize both antigens in this assay, those from the clones initially designated M2DS/DSF10; M7D5/G7; M7D5/AllF7; and M1CS/E7, and hereafter called Fayum, Luxor, Dendera, and Karnak, respectively.

A sample of line Fayum was deposited with the American Type Culture Collection (ATCC), 12301 Parklawn Drive, Rockville, Md. 20852 on Jul. 12, 1991, and was assigned ATCC Accession No. HB10823.

The deposit of clone Fayum was made pursuant to a contract between ATCC and the assignee of this patent application, Board of Supervisors of Louisiana State University and Agricultural and Mechanical College. The contract with ATCC provides for permanent availability of the progency of this clone and cell line to the public on the issuance of the U.S. patent describing and identifying the deposit or the publication or the laying open to the public of any U.S. or foreign patent application, whichever comes first, and for availability of the progeny of this clone and cell line to one determined by the U.S. Commissioner of Patents and Trademarks to be entitled thereto according to 35 U.S.C. § 122 and the Commissioner's rules pursuant thereto (including 37 C.F.R. § 1.14, with particular reference to 886 OG 638). The assignee of the present application has agreed that if the clones or cell line on deposit should die or be lost or destroyed when cultivated under suitable conditions, they will be promptly replaced on notification with a viable culture of the same clone or cell line.

Immunoblots of SDS-PAGE-resolved fresh fluke antigen and *F. hepatica* excretory-secretory product were prepared. Three of the four monoclonal antibodies ( all except that from Karnak) bound a low-molecular-weight band similar to that of the immune sera of the mice used to produce the fusions for production of monoclonal antibodies.

These four monoclonal antibodies, or other antibodies produced through similar means or other means known in the art, may be used singly or in combination to produce an antigen trap test against the Gellah 26 antigen. See, for example, David et al., U.S. Pat. No. 4,376,110; Bestwick et al., U.S. Pat. No. 4,895,804; Yeoman et al., U.S. Pat. No. 4,916,055; and Bartorelli et al., U. S. Pat. No. 4,383,985; the entire disclosures of all of which are incorporated by reference. In general, such tests will combine a sample comprising feces, intestinal content, or bile with the monoclonal antibody, forming an antibody-antigen complex if antigen is present. Typically, the complex will include a detectable label., which may be associated with the antibody or with the antigen. The detectable label may, for example, be radioactive, a fluorophore, a dye, an electron-dense compound, or an enzyme. The antibody may be coupled to an insoluble solid phase. A kit for such an antigen trap test may include the assay materials as stated above, and instructions for their use.

It is expected that the techniques of this invention will also work with other Fasciola species, such as *Fasciola gigantica*, which is a problem principally in tropical and subtropical regions.

We claim:

1. A method for diagnosing *Fasciola hepatica* infection, comprising the steps of:
   (a) combining a sample selected from the group consisting of feces and intestinal content with an antibody which specifically binds Gellah 26 antigen, said antigen being an antigen of *Fasciola hepatica* having a molecular weight of about 26,000 daltons;
   (b) incubating said sample with said antibody for a time and under conditions sufficient for the formation of antibody-Gellah 26 antigen complexes; and
   (c) detecting the presence of said complexes formed in step (b) as an indication of *Fasciola hepatica* infection.

2. A method as recited in claim 1, wherein said sample is collected from a human.

3. A method for diagnosing *Fasciola hepatica* infection, comprising the steps of:
   (a) combining a sample selected from the group consisting of feces and intestinal content with a monoclonal antibody which specially binds Gellah 26 antigen, said antigen being an antigen of *Fasciola hepatica* having a molecular weight of about 26,000 daltons;
   (b) incubating said sample with said antibody for a time and under conditions sufficient for the formation of monoclonal antibody-Gellah 26 a antigen complexes; and
   (c) detecting the presence of said complexes formed in step (b) as an indication of *Fasciola hepatica* infection.

4. A method as recited in claim 3, wherein the complex additionally comprises a detectable label.

5. A method as recited in claim 4, wherein the detectable label is selected from the group consisting of radioactive material, fluorophore, dye, an electron-dense compound, and an enzyme.

6. A method as recited in claim 5, wherein the antibody is detectably labeled.

7. A method as recited in claim 7, wherein said sample is collected from a human.

8. A method as recited in claim 4, wherein said sample is collected from a human.

9. A method as recited in claim 5, wherein said sample is collected from a human.

10. A method as recited in claim 6, wherein said sample is collected from a human.

11. A competitive immunoassay method for diagnosing *Fasciola hepatica* infection by detecting the presence of Gellah 26 antigen comprising the steps of:
   (a) combining a sample selected from the group consisting of feces and intestinal content with a monoclonal antibody which specifically binds Gellah 26 antigen, said antigen being an antigen of *Fasciola hepatica* having a molecular weight of about 26,000 daltons; and a predetermined amount of purified, labeled Gellah 26 antigen, said label being selected from the group consisting of a radioactive material, a fluorophore, a dye, an electron dense compound, and an enzyme;
   (b) incubating said sample, said antibody, and said labelled antigen for a time and under conditions sufficient for said labelled antigen to compete with Gellah 26 antigen present in said sample for binding to said antibody; and
   (c) detecting the amount of said labelled antigen bound to said antibody;

whereby the amount of labelled antigen which is detected is a measure inversely related to the amount of Gellah 26 antigen present in said example.

12. A method as recited in claim 11, wherein said sample is collected from a human.

* * * * *